US012403356B2

(12) United States Patent
Bhatt et al.

(10) Patent No.: US 12,403,356 B2
(45) Date of Patent: Sep. 2, 2025

(54) VOICE THERAPY DEVICE AND SYSTEM

(71) Applicants: DUKE UNIVERSITY, Durham, NC (US); NORTH CAROLINA STATE UNIVERSITY, Raleigh, NC (US)

(72) Inventors: Sandeep Bhatt, Raleigh, NC (US); Dennis Frank-Ito, Durham, NC (US); Kelly A. Umstead, Raleigh, NC (US)

(73) Assignees: DUKE UNIVERSITY, Durham, NC (US); NORTH CAROLINA STATE UNIVERSITY, Raleigh, NC (US)

( * ) Notice: Subject to any disclaimer, the term of this patent is extended or adjusted under 35 U.S.C. 154(b) by 14 days.

(21) Appl. No.: 18/019,574

(22) PCT Filed: Aug. 6, 2021

(86) PCT No.: PCT/US2021/044881
§ 371 (c)(1),
(2) Date: Feb. 3, 2023

(87) PCT Pub. No.: WO2022/032055
PCT Pub. Date: Feb. 10, 2022

(65) Prior Publication Data
US 2024/0325820 A1 Oct. 3, 2024

Related U.S. Application Data

(60) Provisional application No. 63/062,104, filed on Aug. 6, 2020.

(51) Int. Cl.
*A63B 23/18* (2006.01)
(52) U.S. Cl.
CPC .......... *A63B 23/18* (2013.01); *A63B 2220/56* (2013.01); *A63B 2225/09* (2013.01); *A63B 2225/50* (2013.01)

(58) Field of Classification Search
CPC . A63B 23/18; A63B 2220/56; A63B 2225/09; A63B 2225/50; A63B 23/185; A63B 2230/40; A61B 5/097
See application file for complete search history.

(56) References Cited

U.S. PATENT DOCUMENTS 2,175,191 A    10/1939  Goyette
4,221,381 A *   9/1980  Ericson .................. A63B 23/18
                                                            73/239

(Continued)

FOREIGN PATENT DOCUMENTS

CN    207833725 U  *  9/2018
EP       3358564 A1    8/2018

(Continued)

OTHER PUBLICATIONS (AHSA) ASA. The use of voice therapy in the treatment of dysphonia. American Speech-language-hearing association. Website http://www.asha.org/policy/TR2005-00158.htm. Updated 2005, accessed Aug. 15, 2018. 9 pages.

(Continued)

*Primary Examiner* — Nyca T Nguyen
(74) *Attorney, Agent, or Firm* — Casimir Jones, S.C.; Brian F. Bradley

(57) ABSTRACT

A voice therapy device including a body having an internal passageway with a longitudinal axis that defines an airflow direction; a mouthpiece positioned at a proximal end of the body; and a resistance portion positioned at a distal end of the body, where the resistance portion is adjustable to vary an airflow resistance through the internal passageway. In some embodiments, the voice therapy device includes a sensor electrically coupled to a processor. A system for voice therapy includes the voice therapy device and a software application.

20 Claims, 9 Drawing Sheets

(56) References Cited

U.S. PATENT DOCUMENTS

| | | | |
|---|---|---|---|
| 4,378,724 A | 4/1983 | Lamart | |
| 4,739,987 A | 4/1988 | Nicholson | |
| 5,249,499 A | 10/1993 | Goldstein et al. | |
| 5,451,190 A | 9/1995 | Liardet | |
| 5,454,375 A * | 10/1995 | Rothenberg | A61B 5/087 |
| | | | 73/23.3 |
| 6,030,350 A * | 2/2000 | Jiang | A61B 5/4082 |
| | | | 600/23 |
| 6,083,141 A | 7/2000 | Hougen | |
| 8,975,499 B1 | 3/2015 | Stoutenborough et al. | |
| 10,780,318 B1 * | 9/2020 | Ghazzawi | A63B 23/18 |
| 11,571,605 B2 * | 2/2023 | Chesbrough | A63B 23/18 |
| 11,937,914 B2 * | 3/2024 | Grudin | A61B 5/087 |
| 2003/0140925 A1 | 7/2003 | Sapienza et al. | |
| 2012/0272956 A1 | 11/2012 | Rusher | |
| 2015/0258370 A1 * | 9/2015 | Arkush | A61B 5/087 |
| | | | 482/8 |
| 2016/0128863 A1 * | 5/2016 | Loomas | A61M 15/002 |
| | | | 128/848 |
| 2017/0348504 A1 | 12/2017 | Denizoglu | |
| 2018/0050169 A1 | 2/2018 | Denizoglu | |
| 2018/0236301 A1 * | 8/2018 | Jones | A61M 16/208 |
| 2019/0299055 A1 | 10/2019 | Poulsen et al. | |
| 2021/0353889 A1 * | 11/2021 | Carroll | A61M 16/1055 |
| 2023/0218945 A1 * | 7/2023 | Boder | A63B 23/18 |
| | | | 482/10 |
| 2023/0285800 A1 * | 9/2023 | Perre | A63F 13/24 |
| 2023/0321375 A1 * | 10/2023 | Cegla | A61M 16/20 |
| | | | 128/200.24 |

FOREIGN PATENT DOCUMENTS

| | | | | |
|---|---|---|---|---|
| GB | 2530397 A * | 3/2016 | | A61M 16/0006 |
| JP | 2017167480 | 9/2017 | | |
| WO | WO-0078407 A1 * | 12/2000 | | A63B 23/18 |
| WO | WO 2016/105310 | 6/2016 | | |
| WO | WO 2019/161065 | 8/2019 | | |

OTHER PUBLICATIONS

Andrade et al., Electroglottographic study of seven semi-occluded exercises: LaxVox, straw, lip-trill, tongue-trill, humming, hand-over- mouth, and tongue-trill combined with hand-over-mouth. J Voice. Sep. 2014;28(5):589-95.

Andrade et al., The Flow and Pressure Relationships in Different Tubes Commonly Used for Semi-occluded Vocal Tract Exercises. J Voice. Jan. 2016;30(1):36-41.

Behrman. Speech and voice science. 3rd ed. Sand Diego: Plural Publishing, Inc; 2017. TOC only. 3 pages.

Strengthen respiratory muscles, reduce shortness of breath and promote safer swallow. www.pnmedical.com/product/the-breather/ Retrieved from the internet Oct. 30, 2023. 26 pages.

Cohen et al., Development and validation of the Singing Voice Handicap-10. Laryngoscope. Sep. 2009;119(9):1864-9.

Cohen et al., Direct health care costs of laryngeal diseases and disorders. Laryngoscope. Jul. 2012;122(7):1582-8.

Cohen et al., Otolaryngology utilization of speech-language pathology services for voice disorders. Laryngoscope. Apr. 2016;126(4):906-12.

Cohen et al., Prevalence and causes of dysphonia in a large treatment-seeking population. Laryngoscope. Feb. 2012;122(2):343-8.

Cohen et al., Treatment responsiveness of the Singing Voice Handicap Index. Laryngoscope. Sep. 2008;118(9):1705-8.

Desjardins et al., A Systematic Review of Voice Therapy: What "Effectiveness" Really Implies. J Voice. May 2017;31(3):392.e13-392.e32. 20 pages.

DoctorVOX Voice Therapy Complete Set. www.Amazon.com/doctorvox-voice-therapy-complete-set/dp/b077grpbtx. Retrieved from the internet Aug. 25, 2023. 3 pages.

DoctorVOX, Devices for Vocal Fitness. www.Doctorvox.com. Retrieved from the internet Aug. 25, 2023. 3 pages.

EMST 150 (Aspire Products LLC) Retrieved from the internet Aug. 25, 2023. 2 pages.

Fu et al., Intensive versus traditional voice therapy for vocal nodules: perceptual, physiological, acoustic and aerodynamic changes. J Voice. Mar. 2015;29(2):260.e31-44.

Guzman et al., Efficacy of Water Resistance Therapy in Subjects Diagnosed With Behavioral Dysphonia: A Randomized Controlled Trial. J Voice. May 2017;31(3):385.e1-385.e10.

Half a billion plastic straws are used and discarded every day, what an unacceptable wste. Los Angeles Times (online) Jan. 17, 2018. 5 pages.

International Search Report and Written Opinion for PCT/US21/44881. Mailed Nov. 9, 2021. 12 pages.

Jones et al., Respiratory muscle training (RMT) in late-onset Pompe disease (LOPD): A protocol for a sham-controlled clinical trial. Molecular Genetics and Metabolism. 2019, 127, 346-354.

Kapsner-Smith et al., A Randomized Controlled Trial of Two Semi-Occluded Vocal Tract Voice Therapy Protocols. J Speech Lang Hear Res. Jun. 2015;58(3):535-49.

McCullough, Treating laryngeal hyperfunciton with flow phonation. clinicatrials.gov. 2016. Retrieved from the internet Aug. 25, 2023. 7 pages.

Meerschman et al., Short-Term Effect of Two Semi-Occluded Vocal Tract Training Programs on the Vocal Quality of Future Occupational Voice Users: "Resonant Voice Training Using Nasal Consonants" Versus "Straw Phonation". J Speech Lang Hear Res. Sep. 18, 2017;60(9):2519-2536.

Oovo Vocal Straw. https://oovostraw.com. Retrieved from the internet Aug. 25, 2023. 5 pages.

Scearce. Manual of singing voice rehabilitation: A practical approach to vocal health and wellness. 1st ed. Sand Diego. Plural Publising, inc: 2016. TOC only. 7 pages.

Smith et al., Patient factors related to voice therapy attendance and outcomes. J Voice. Nov. 2010;24(6):694-701.

Speyer. Effects of voice therapy: a systematic review. J Voice. Sep. 2008;22(5):565-80.

Sulica et al., Management of benign vocal fold lesions: a survey of current opinion and practice. Ann Otol Rhinol Laryngol. Oct. 2003;112(10):827-33.

Titze. Voice training and therapy with a semi-occluded vocal tract: rationale and scientific underpinnings. J Speech Lang Hear Res. Apr. 2006;49(2):448-59.

Tyrmi et al., Resonance Tube or Lax Vox? J Voice. Jul. 2017;31(4):430-437.

Warner. Why do stars like adele keep losing their voice? The Guardian.—08-10T05:01:28.000Z 2017.

Won et al., The prevalence and factors associate with vocal nodules in general population: Cross-sectional epidemiological study. Medicine. 2016;95(35):e4971. 1-6.

Menzes, KKP et al. A Review on Respiratory Muscle Training Devices, J Pulm Respir Med 2018, 8:2, 7 pages.

Saccente-Kennedy, B. et al. A Pilot Study Assessing the Therapeutic Potential of a Vibratory Positive Expiratory Pressure Device (Acapella Choice) in the Treatment of Voice Disorders, Journal of Voice, vol. 34, No. 3, 2020, 10 pages.

Acevedo, K. et al. Remote Voice Therapy With an Oscillatory Positive Expiratory Pressure Device in Subjects With Vocal Fatigue: A Randomized Controlled Trial, Journal of Speech, Language, and Hearing Research vol. 66 4801-4811 Dec. 2023.

EP Search Report, EP Patent Application No. 21853043.4, dated Jun. 10, 2024, 8 pages.

* cited by examiner

VOICE THERAPY DEVICE AND SYSTEM

CROSS-REFERENCE TO RELATED APPLICATIONS

This application claims priority to U.S. Provisional Patent No. 63/062,104 filed on Aug. 6, 2020, the entire contents of which are incorporated herein by reference.

BACKGROUND

Many people suffer from problems associated with voice production, which can be caused by a variety of common causes. This can lead to negative effects such as reduced physical and mental health, reduced quality of life, and loss of livelihood. To address the problem of dysphonia and other vocal disorders, therapy is often suggested as one approach to recovery. This may include voice exercises to strengthen or train the organs associated with speech.

One such therapy is semi-occluded vocal tract exercises (SOVTE). In this approach, a patient phonates through a straw, which creates external, downward pressure on the vocal folds, reducing vocal fold fatigue through more efficient vibration and minimizing collision forces. The patient works with a clinician, typically a speech-language pathologist (SLP), to execute a rehabilitative or preventative vocal training regime. Common drinking straws are frequently used for SOVTE. While these can be very effective, they can be inconsistent, do not provide measurable information, and are not reusable over a long term. Hence, there is an ongoing need for improved devices and methods for vocal disorder therapy.

SUMMARY

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

One aspect of the present disclosure provides a voice therapy device, comprising, consisting of, or consisting essentially of a body having an internal passageway with a longitudinal axis that defines an airflow direction; a mouthpiece positioned at a proximal end of the body; and a resistance portion positioned at a distal end of the body, where the resistance portion is adjustable to vary an airflow resistance through the internal passageway.

In some embodiments, the resistance portion includes a blocking structure and one or more airflow outlets.

In some embodiments, the blocking structure is symmetrical about the longitudinal axis.

In some embodiments, the airflow outlets are oriented perpendicular to the airflow direction, and/or airflow exits from the airflow outlets in a substantially uniform pattern about the longitudinal axis.

In some embodiments, the blocking structure is conical and a height of the blocking structure is greater than a widest diameter of the blocking structure.

In some embodiments, the resistance portion is a cap positioned at least partially around the body.

In some embodiments, the device is configured to provide backpressure to a user's vocal folds during phonation.

In some embodiments, the mouthpiece and/or the resistance portion are removably connected to the body.

In some embodiments, the airflow resistance is varied by adjusting an open area between the resistance portion and the body.

In some embodiments, the airflow resistance is continuously adjustable between a minimum resistance and a maximum resistance.

In some embodiments, the device comprises a threaded connection between the resistance portion and the body, where the airflow resistance is adjusted by rotating the resistance portion relative to the body.

In some embodiments, the body include indicia representing a level of airflow resistance, and wherein the resistance portion includes an indicator corresponding to the indica.

In some embodiments, the device comprises a pressure sensor in fluid communication with the internal passageway and in electronic communication with a processor.

In some embodiments, the processor is coupled to a first mount formed on the body and a battery is coupled to a second mount formed on the body.

In some embodiments, the device comprises a wireless communication module in electronic communication with the processor.

Another aspect of the present disclosure provides a system for voice therapy, comprising, consisting of, or consisting essentially of a device according to the present disclosure and a software application.

In some embodiments, the software application comprises at least one of vocal education tools; vocal analysis; vocal rehabilitation tools, and vocal lifestyle support features.

In some embodiments, the software application provides real time user feedback based on pressure sensor data.

In some embodiments, the software application is on an external device.

Another aspect of the present disclosure provides a method of voice therapy, comprising performing prescribed phonation and/or breathing exercises using a device or system according to the present disclosure.

The present disclosure describes a device and method to support vocal therapy. The device is particularly useful for straw phonation for semi-occluded vocal tract exercises (SOVTEs). The device includes a resistance portion that can be adjusted to provide variable back pressure.

Other aspects of the disclosure will become apparent by consideration of the detailed description and accompanying drawings.

BRIEF DESCRIPTION OF THE DRAWINGS

The accompanying figures and examples are provided by way of illustration and not by way of limitation. The foregoing aspects and other features of the disclosure are explained in the following description, taken in connection with the accompanying example figures (also "FIG.") relating to one or more embodiments.

Figure 1:
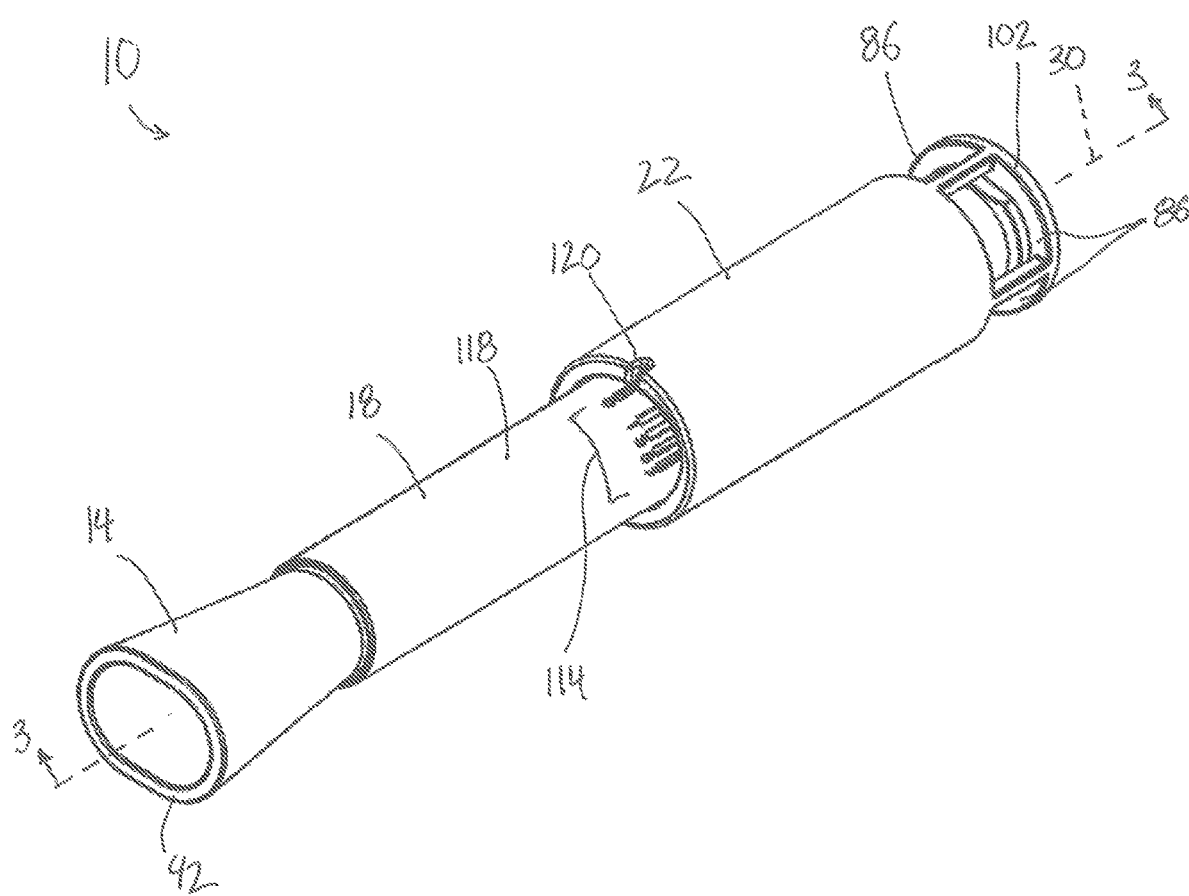
FIG. 1 is a perspective view of a device for voice therapy.

Before any embodiments are explained in detail, it is to be understood that the invention is not limited in its application to the details of construction and the arrangement of components set forth in the following description or illustrated in the following drawings. The invention is capable of other embodiments and of being practiced or of being carried out in various ways.

DETAILED DESCRIPTION

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e., at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that an apparatus comprises components A, B, and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

The term "effective amount" or "therapeutically effective amount" refers to an amount sufficient to effect beneficial or desirable biological and/or clinical results.

As used herein, the term "subject" and "patient" are used interchangeably herein and generally refer to humans. In some embodiments, the subject comprises a human who is undergoing voice therapy with a device as prescribed herein.

Unless otherwise defined, all technical terms used herein have the same meaning as commonly understood by one of ordinary skill in the art to which this disclosure belongs.

According to one aspect of the present disclosure, devices and methods to support vocal therapy are described. The device is particularly useful for straw phonation semi-occluded vocal tract exercises (SOVTEs), which are used in voice therapy and training and which are an integral component of clinical voice therapy regimens. In some embodiments, the device is a modular device that has a removable mouthpiece and which can be adjusted to provide varying back pressure to the vocal folds. The disclosed voice therapy device addresses the needs of vocal professionals during rehabilitation and to support the proactive prevention of vocal injury.

Current approaches for straw phonation often use conventional disposable drinking straws of various diameters. These straws do not allow a user to easily vary the back-pressure generated in the vocal tract, nor to increase or decrease the difficulty of the therapeutic exercise. Feedback from speech-language pathologists indicates that this customizability would be highly advantageous to patients.

The device disclosed herein can replace an unintentional therapeutic device (drinking straws) with one whose functionality is specifically targeted to support SOVTEs. In some cases, the device can be used either with or without the guidance of a speech-language pathologist. The device has the potential to make SOVTEs accessible to millions of professional voice users (such as teachers, call center workers, receptionists, counselors, dispatchers, trial lawyers, broadcasters, etc.) who suffer from dysphonia but who have not had the opportunity to include a voice care regimen into their daily lives, or those who wish to prevent the potential onset of vocal cord injury. Additionally, while there are some devices currently available for respiratory therapy, many such devices target muscle groups. Unlike these devices, the device disclosed herein is designed to improve efficiency of voice production through more efficient oscillation of the vocal folds. Further, the device can foster an improved clinical relationship between a voice therapist and a patient.

With reference to FIG. 1, a device 10 for voice therapy includes a mouthpiece 14, a body 18, and a resistance portion 22. In the illustrated embodiment, the resistance portion 22 is a cap (e.g., a resistance cap). In the illustrated embodiment, the body 18 is configured to be removably connected to the mouthpiece 14 and the resistance portion 22. In some embodiments, the mouthpiece 14, the body 18, and the resistance portion 22 are modular, interchangeable parts. In other embodiments, some (or all of) the components are combined or integrated into a single part. As explained in further detail herein, the device 10 is configured to provide backpressure to a user's vocal folds during phonation.

Figure 2:
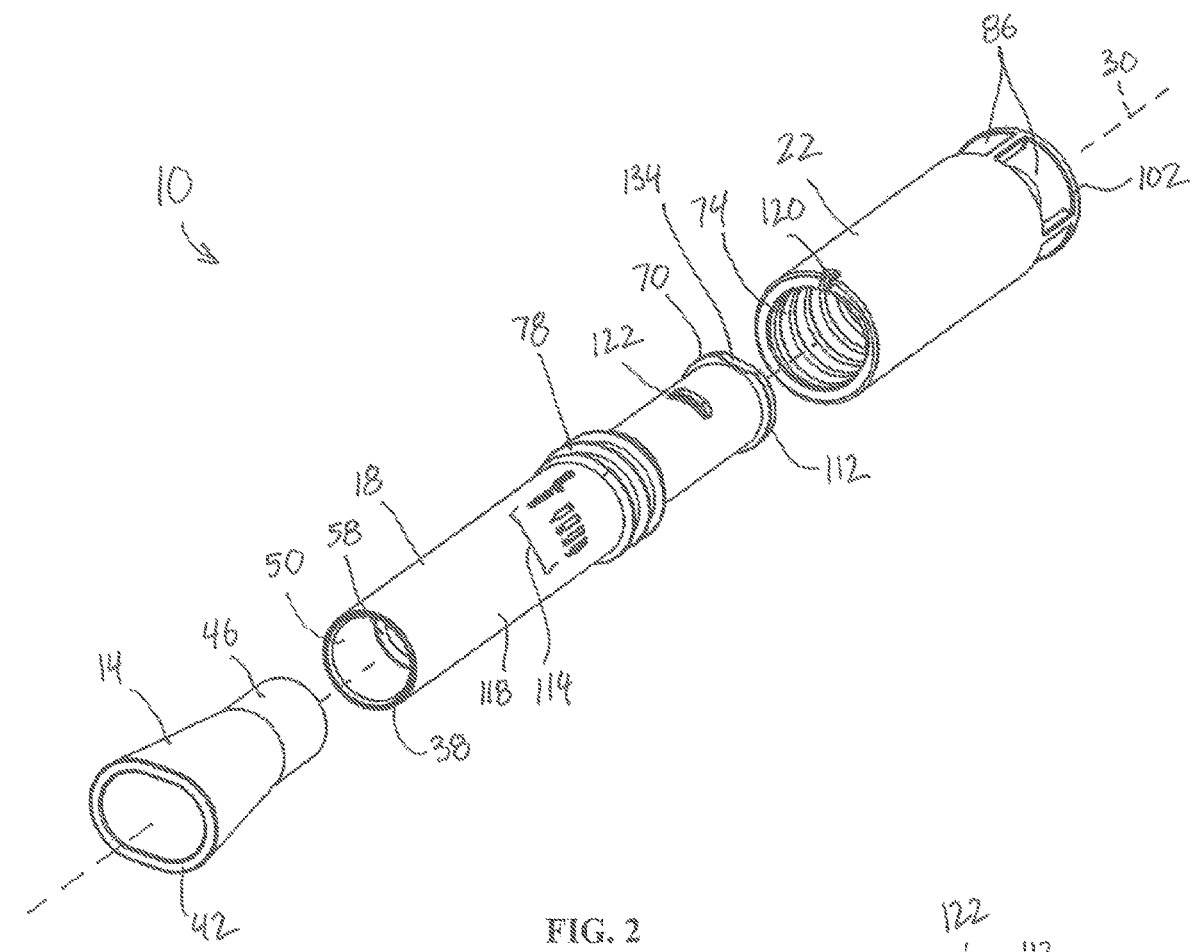
FIG. 2 is an exploded view of the device of FIG. 1.
Figure 3:
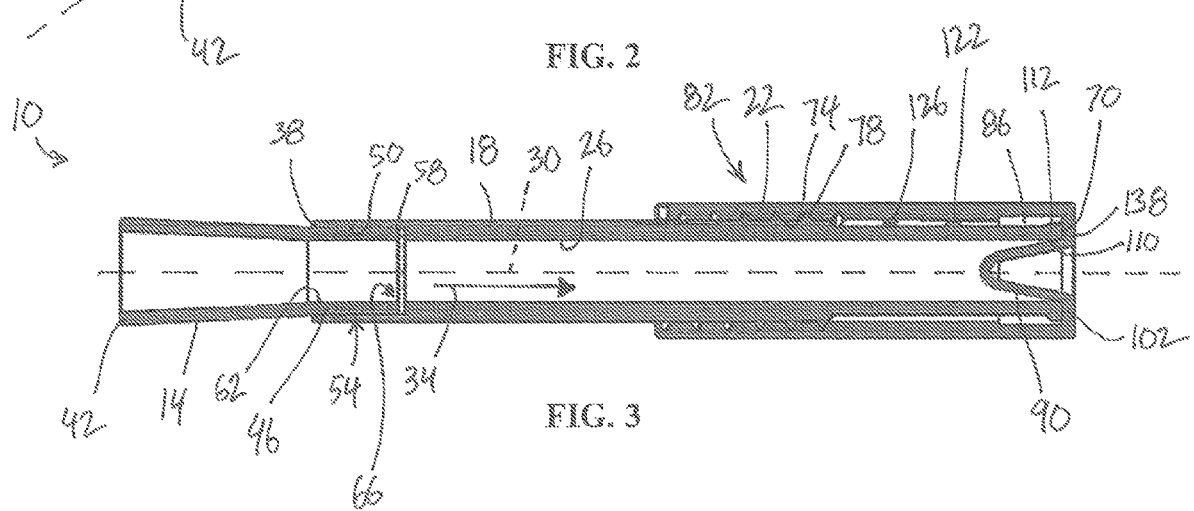
FIG. 3 is a cross-sectional view of the device of FIG. 1, taken along lines 3-3 shown in FIG. 1.

With reference to FIGS. 2 and 3, the body 18 has an internal passageway 26 with a longitudinal axis 30 that defines an airflow direction 34. In other words, the internal passageway 26 in the body 18 is in fluid communication with the resistance portion 22 and the mouthpiece 14. In the illustrated embodiment, the airflow direction 34 extends from the mouthpiece 14 towards the resistance portion 22. In some embodiments, the internal passageway 26 is any suitable shape and extends into the mouthpiece 14 and/or the resistance portion 22. In some embodiments, the body 18 has a contoured shape to provide an overall ergonomic shape for improved handling.

With continued reference to FIGS. 2 and 3, the mouthpiece 14 is positioned at a proximal end 38 of the body 18. The mouthpiece 14 includes a mouth end 42 that has a shape that facilitates a good seal between a patient's lips and the device 10 while also encouraging a relaxed mouth posture. In the illustrated embodiment, a stem 46 of the mouthpiece 14 is removably received within a bore 50 formed in the proximal end 38 of the body 18. In other embodiments, the stem 46 of the mouthpiece 14 is positioned around the proximal end 38 of the body 18. In the illustrated embodiment, the mouthpiece 14 is coupled to the body 18 by an interference fit 54 and a shoulder 58 stop. In the illustrated embodiment, an internal passageway 62 of the mouthpiece 14 creates a smooth transition 66 to the internal passageway 26 of the body 18. In other embodiments, the mouthpiece 14 is coupled to the body 18 in any suitable fashion, such as a friction fit, a snap lock, a twist lock, threads, etc.

Figure 6:
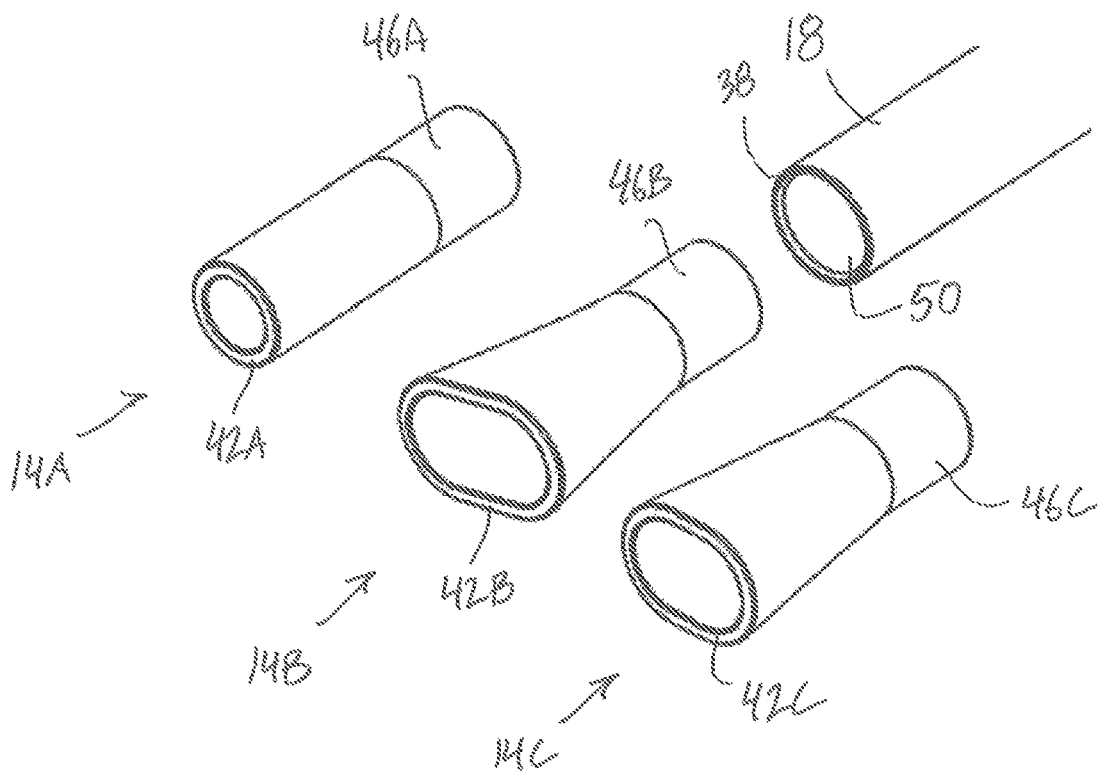
FIG. 6 is a partial exploded view of the device of FIG. 1, shown with alternative mouthpieces.
Figure 7:
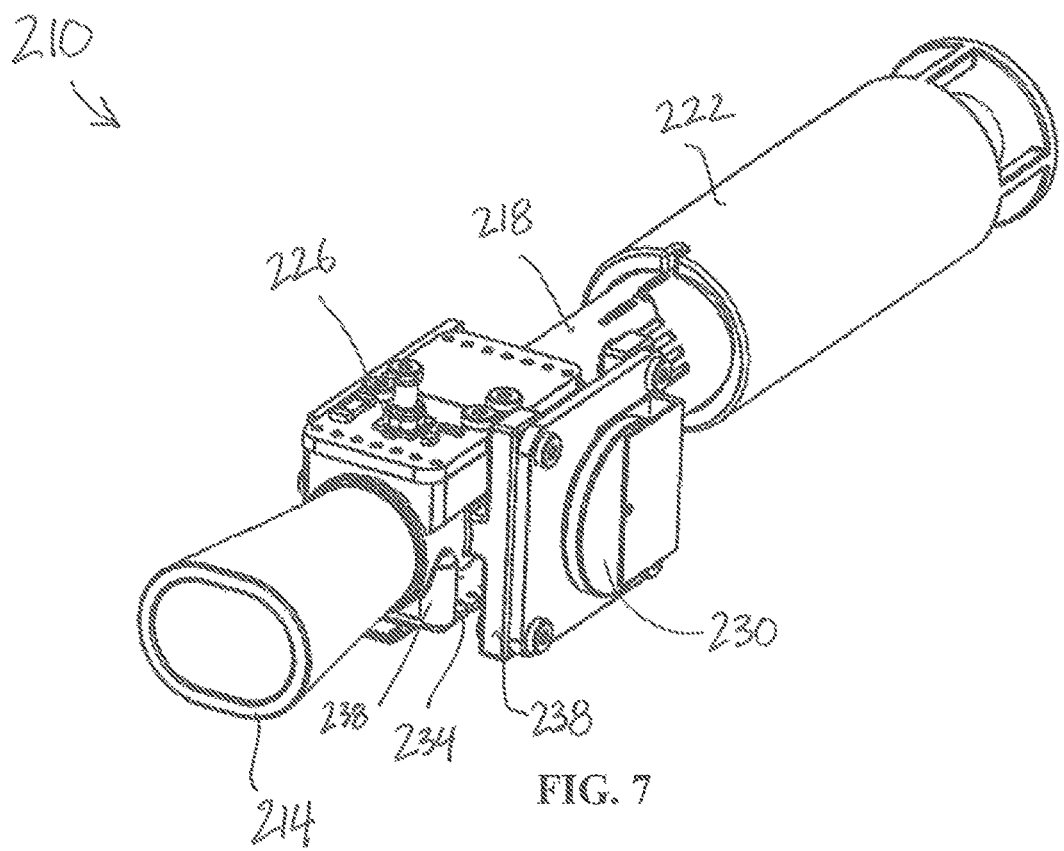
FIG. 7 is a top perspective view of a device for voice therapy according to another embodiment.
Figure 8:
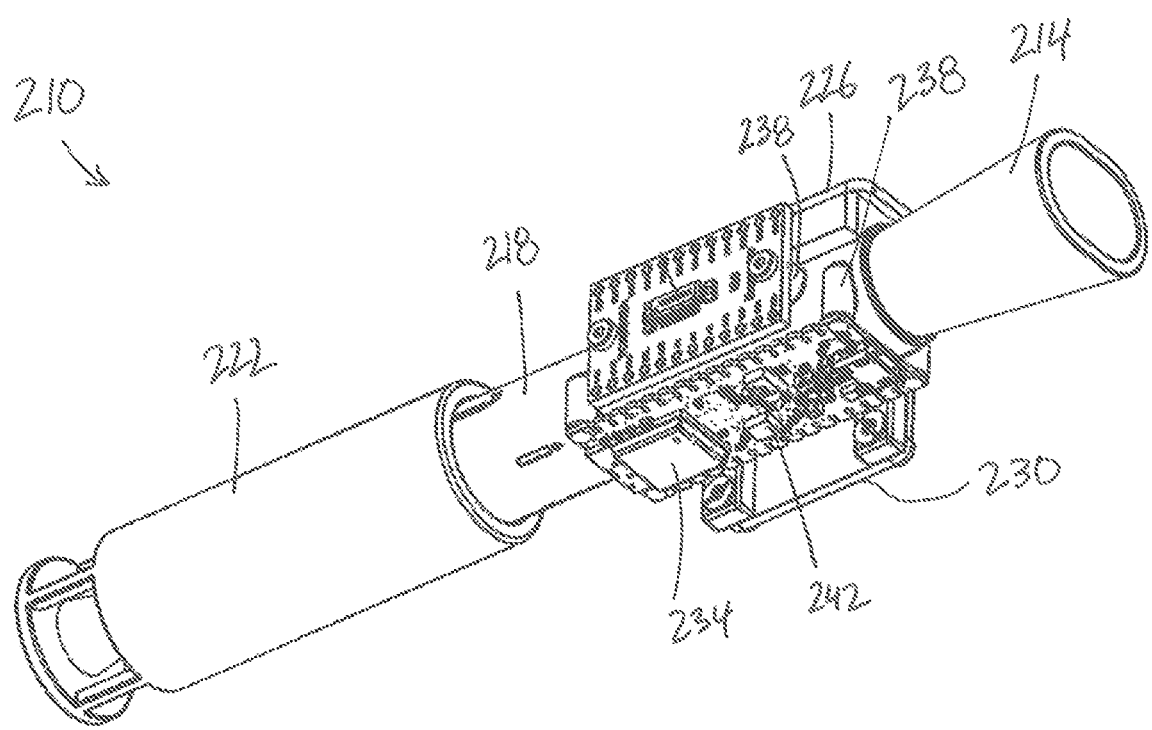
FIG. 8 is a bottom perspective view of the device of FIG. 7.

With reference to FIG. 6, the device 10 includes a plurality of interchangeable mouthpieces 14A, 14B, 14C. Each of the mouthpieces 14A-14C includes a stem 46A-46C removably received within the bore 50 of the body 18. Each of the mouthpieces 14A-14C includes a different sized opening at a mouth end 42A-42C to accommodate different mouth sizes, facial shapes, embouchure strength, etc. The various sized mouthpieces 14A-14C accommodate for different mouth sizes and preferences, while also allowing for closure of the lips without creating too much tension in the lip or facial muscles. In some embodiments, the interchangeable mouthpiece is an over-the-mouth mask. In other embodiments, the interchangeable mouthpiece is an over-the-nose-and-mouth mask. In other embodiments, the interchangeable mouthpiece is a face mask. Various interchangeable mouthpieces, such as mouthpieces 14A-14C, make the device 10 relevant not just to SOVTEs but to other various speech, and speech adjacent therapies and exercises.

With reference to FIGS. 2 and 3, the resistance portion 22 is positioned at a distal end 70 of the body 18. In the illustrated embodiment, the resistance portion 22 is positioned opposite the mouthpiece 14. In the illustrated embodiment, the resistance portion 22 is a cap (cap shaped) positioned at least partially around the body 18. In other embodiments, the resistance portion is received within the body. As explained further herein, the resistance position 22 is adjustable (e.g., manually adjustable by an operator or user) to vary an airflow resistance through the internal passageway 26 of the body 18.

Figure 4A:
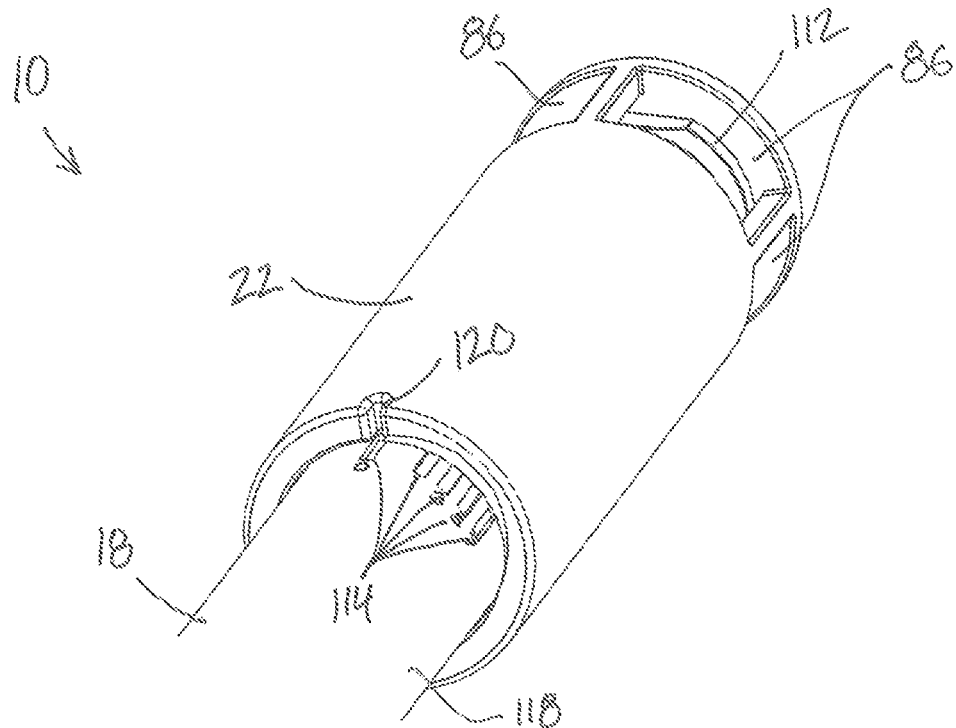
FIG. 4A is a partial perspective view of the device of FIG. 1 in a first configuration (a first airflow resistance setting).
Figure 4B:
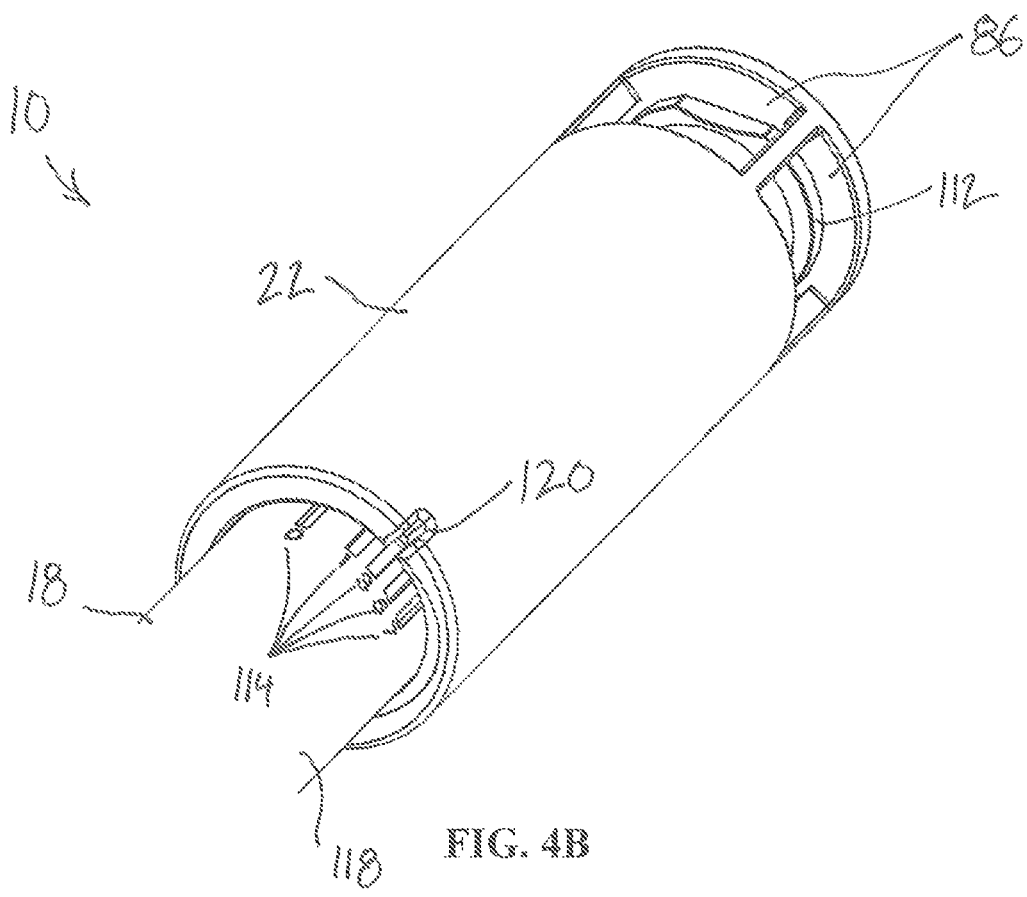
FIG. 4B is a partial perspective view of the device of FIG. 1 in a second configuration (a second airflow resistance setting).

In the illustrated embodiment, the airflow resistance through the device 10 is adjusted by rotating the resistance portion 22 relative to the body 18, about the axis 30. The resistance portion 22 further includes an adjustable connector portion 74 (e.g., a threaded bore) that corresponds to a connector portion 78 (e.g., threads) formed on the body 18. In some embodiments, the connector portion 78 on the body 18 are wide-pitch threads. In other words, a threaded connection 82 (the combination of the threads 78 and the threaded bore 74) is formed between the resistance portion 22 and the body 18. With reference to FIGS. 4A and 4B, the threaded connection 82 creates relative displacement between the body 18 and the resistance portion 22, as the resistance portion 22 is rotated about the axis 30. In other words, rotation of the resistance portion 22 causes the resistance portion 22 to move either closer or further away from the body 18 along the axis 30.

In the illustrated embodiment, the threaded connection 82 provides an adjustable displacement within a range of approximately 8 mm to approximately 12 mm. In some embodiments, the threaded connection 82 provides an adjustable displacement of approximately 10 mm. In the illustrated embodiment, the threaded connection 82 has a turning span within a range of approximately 360 degrees to approximately 1080 degrees. In some embodiments, the threaded connection 82 has a turning span of approximately 720 degrees. In some embodiments, the threaded connection 82 provided approximately 10 mm of adjustable displacement with a turning span of approximately 720 degrees.

With reference to FIGS. 2 and 5A-5C, the resistance portion 22 includes one or more airflow outlets 86 and a blocking structure 90 that impedes the outflow of the patient's breath. In the illustrated embodiment, the blocking structure 90 is symmetrical about the longitudinal axis 30. The one or more airflow outlets 86 are oriented perpendicular to the airflow direction 34. In other words, the one or more airflow outlets 86 are positioned radially outward from, and circumferentially around, the blocking structure 90. In the illustrated embodiment, the blocking structure 90 is conical (a cone, cone-shaped). In some embodiments, the blocking structure 90 is rounded. In other embodiments, the blocking structure 90 is shuttlecock shaped. In the illustrated embodiment, the blocking structure 90 includes a height 94 that extends from a surface 98 of an end portion 102 of the resistance portion 22. In some embodiments, the height 94 of the blocking structure 90 is greater than a widest diameter 106 of the blocking structure 90. The shape of the blocking structure 90 provides a range of airflow resistance values that mimics a usable range for phonation exercises. In addition, the shape of the blocking structure 90 encourages symmetric and stable airflow, which can reduce undesirable flow phenomena such as recirculation and turbulence. In other words, the airflow travels over the blocking structure 90 and exits the outlets 86 in a substantially uniform pattern about the longitudinal axis 30.

Figure 5A:
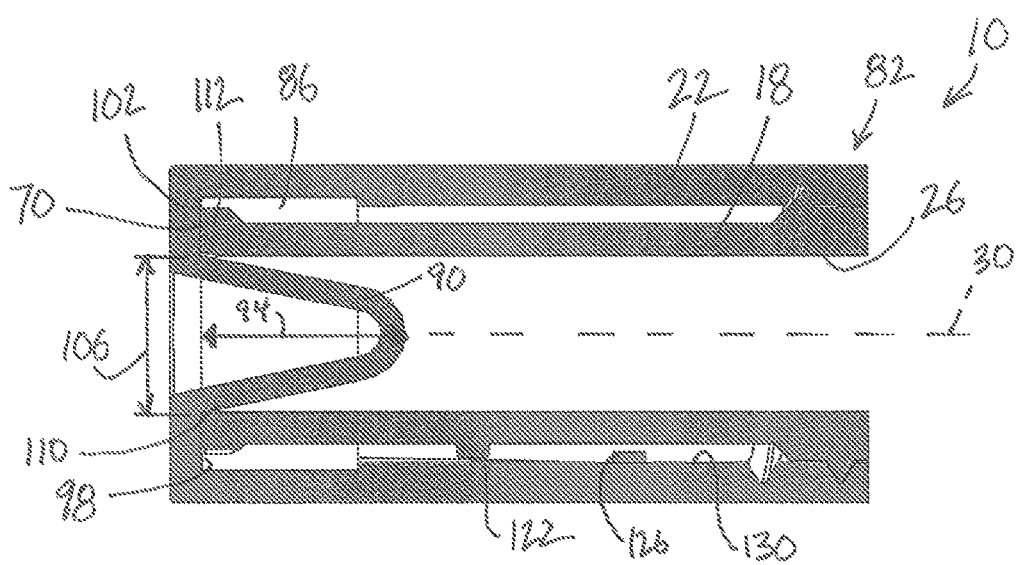
FIG. 5A is a partial cross-sectional view of the device of FIG. 1 in a minimum airflow (maximum resistance) configuration.
Figure 5B:
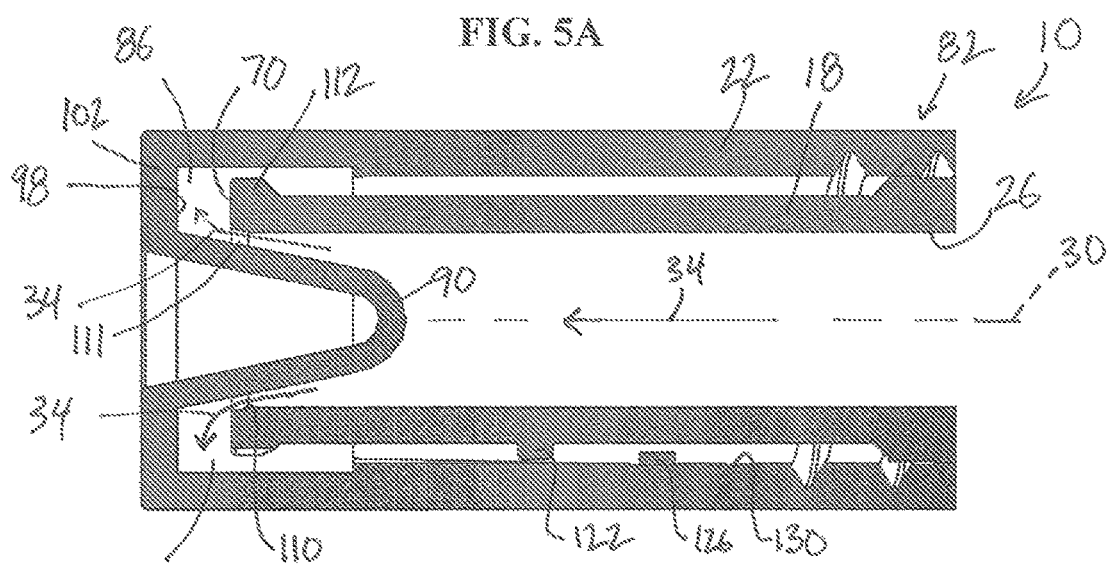
FIG. 5B is a partial cross-sectional view of the device of FIG. 1 in an intermediate airflow (intermediate resistance) configuration.
Figure 5C:
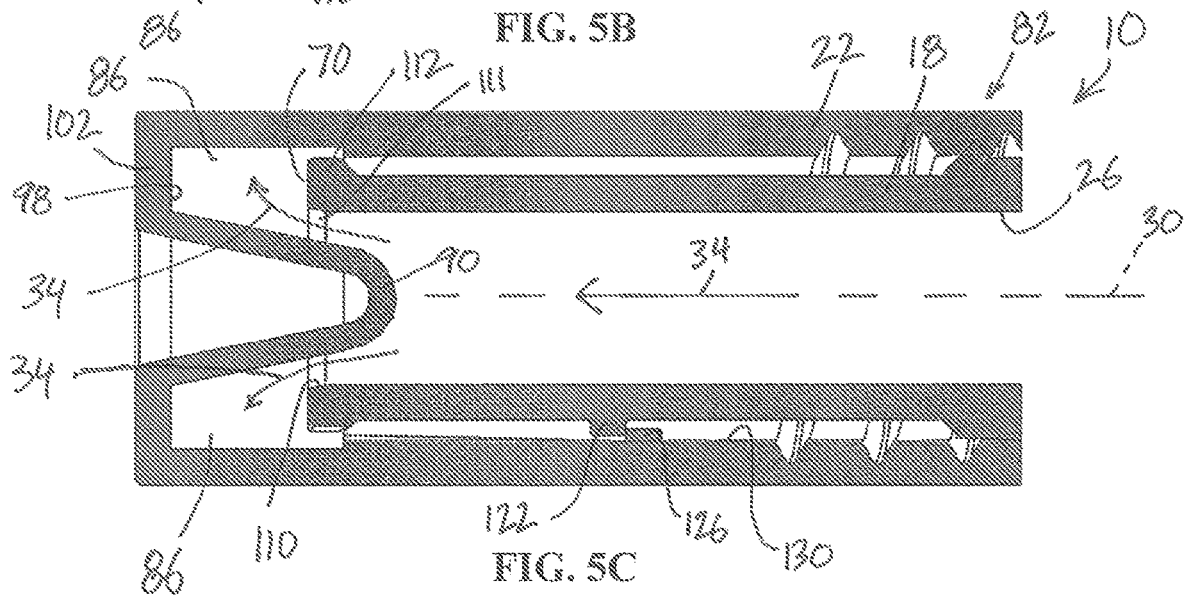
FIG. 5C is a partial cross-sectional view of the device of FIG. 1 in a maximum airflow (minimum resistance) configuration).

With reference to FIGS. 5A-5C, the blocking structure 90 is adjustably positioned through an opening 110 in the distal end 70 of the body 18, extending into the internal passageway 26. The body 18 includes a lip 112 that is substantially the same size as an internal diameter of the resistance portion 22. The airflow resistance through the device 10 is varied by adjusting an open area 111 (e.g., a gap) between the resistance portion 22 and the body 18. In other words, an adjustable variable gap is formed between the body 18 and the resistance portion 22 to create adjustable airflow resistance. In the illustrated embodiment, the open area 111 is defined between the blocking portion 90 and the lip 112. For example, the larger the open area 111, the less airflow resistance through the device 10. Advantageously, the airflow resistance can be varied by a user while the device is in use, allowing a dynamic adjustment without the need to interrupt a therapeutic exercise.

The airflow resistance is continuously adjustable between a minimum resistance (e.g., FIG. 5C), an intermediate resistance (e.g., FIG. 5B), and a maximum resistance (e.g., FIG. 5A). Unlike discrete resistance values, a continuous range of airflow resistance values allows for adjustment to an ideal or optimized airflow resistance for any given user. In some embodiments, the maximum resistance corresponds to zero airflow through the device 10 (i.e., 100% blocked) (FIG. 5A). In some embodiments, a detent holds the device 10 in the completely closed position, which can be useful for storage or travel, for example. In other words, the range of airflow resistance encompasses a continuous range of values from completely closed (i.e., no airflow) through fully open. In some embodiments, the fully open position includes removal of the resistance portion 22 entirely from the body 18.

In some embodiments, the device 10 provides resistances to the airflow in the internal passageway 26 within a range of approximately 0.2 Pa·s/mL to approximately 9.1 Pa·s/mL. In some embodiments, the pressure within the device 10 during operation is within a range of approximately 0 Pa to approximately 1130 Pa. In other embodiments, the rate of airflow through the device 10 during operation is within a range of approximately 0 L/min to approximately 110 L/min.

With reference to FIGS. 4A-4B, the body 18 includes indicia 114 (e.g., fiducial or reference markings) on an outer surface 118 representing a level of the airflow resistance through the device 10. In other words, the indicia 114 provide visual and/or tactile feedback to the user as to the degree of resistance through the device 10. In the illustrated embodiment, the indicia 114 include lines with numbers 1-12 arranged in two rings around the body 18. A corresponding indicator 120 formed in the resistance portion 22 indicates which of the indicia 114 on the body 18 corresponds to the current configuration of the device 10. In the illustrated embodiment, the indicator 120 is a notch. In other embodiments, the indicator is a raised marking, a window marking, and/or a decal or printed marking.

With reference to FIGS. 2 and 5A-5C, a flange 122 is positioned on the outer surface 118 of the body 18 and corresponds to a flange 126 positioned on an inner surface 130 of the resistance portion 22. As the resistance portion 22 is adjusted to a max open position (e.g., FIG. 5C), the flanges 122, 126 abut to create a stop. To accommodate the flange 126, the lip 112 at the distal end 70 of the body 18 includes a flat portion 134.

The ability to fully remove the mouthpiece 14 and the resistance portion 22 facilitates easy cleaning of the device 10. The device 10 can be made, for example, from biocompatible materials such as polycarbonate or ABS plastic, aluminum, stainless steel, etc. As such, the device 10 is simple to assemble, durable, and reusable, and it can be cleaned with soap and water.

In some embodiments, the device 10 includes ergonomic features (e.g., to aid in gripping and handling the device). For example, the body 18 in some embodiments includes a flattened and/or texturized area for fingers to rest. In alternative embodiments, the body includes ribs and/or indentations. Similarly, the resistance portion 22 in some embodiments includes ribs, recesses, texturizations, etc. to provide visual or tactile cues for usage, cleaning, etc.

In the illustrated embodiment, the end portion 102 of the resistance portion 22 provides a surface 138 to rest the device 10 in an upright orientation, with the mouthpiece 14 in the air (i.e., the longitudinal axis 30 vertically oriented). This advantageously avoids the mouthpiece 14 from contact any surfaces, thereby improving sanitation.

With reference to FIGS. 7-10, a device 210 for vocal therapy according to another embodiment is illustrated. The device 210 includes a mouthpiece 214, a body 218, and a resistance portion 222 (similar to components of the device 10). Like the device 10, the device 210 is configured to provide continuous adjustment of airflow resistance through the device 210.

Figure 9:
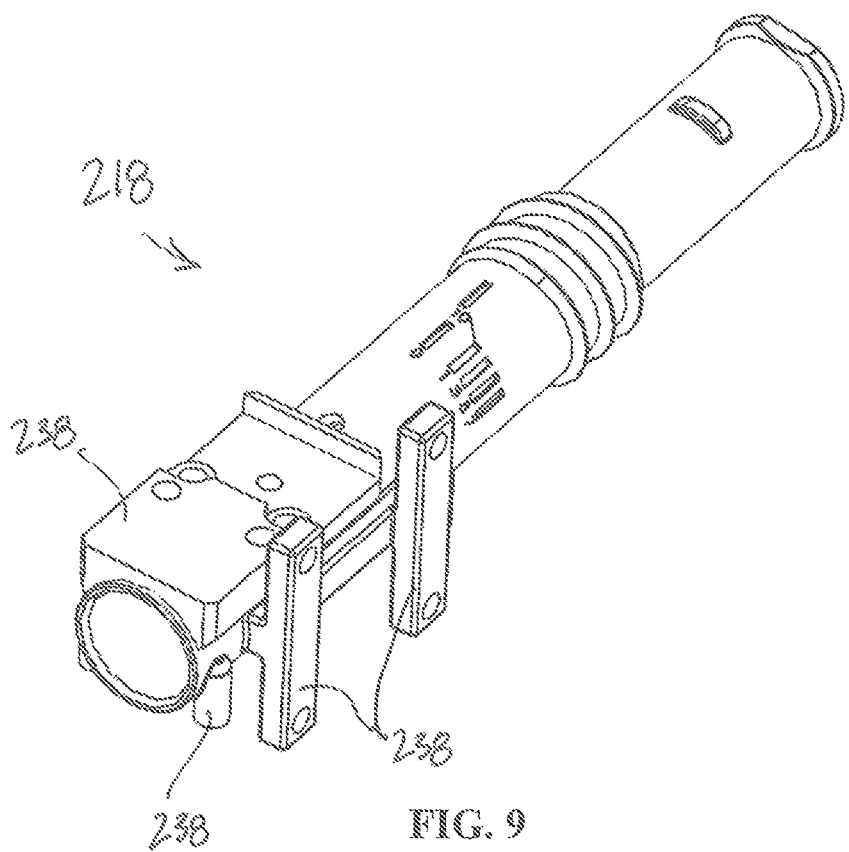
FIG. 9 is a perspective view of a body of the device of FIG. 7.

The device 210 further includes one or more sensors 226 to measure exhalation, phonation, or other related pressures. In the illustrated embodiment, the device 210 also includes a battery 230 and a processor 234 in electrical communication with the battery 230 and the sensor 226. With reference to FIG. 9, the body 218 includes a plurality of mounts 238 formed as an integral part of the body 218. The battery 230, the processor 234, the sensor 226, etc. are positioned on the mounts 238 and secured to the body 218 (e.g., with a fastener). In this case, the device 210 can be referred to as a "smart" voice therapy device.

Figure 10:
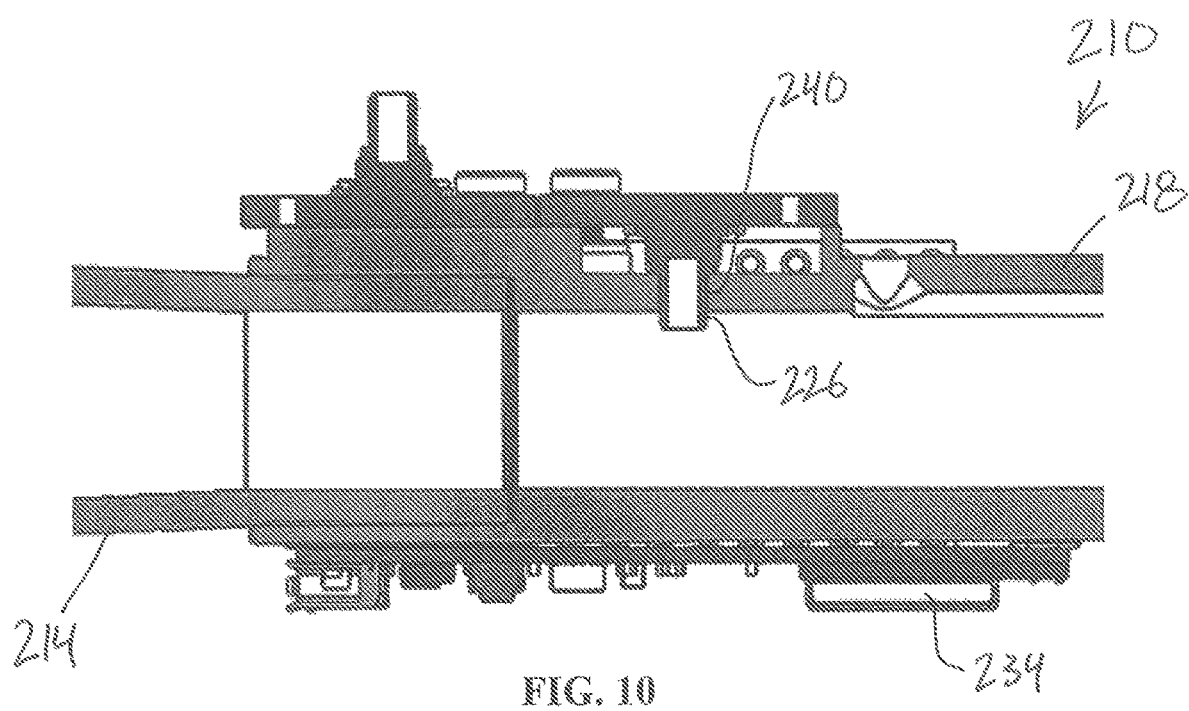
FIG. 10 is a partial cross-sectional view of the device of FIG. 7.

With reference to FIG. 10, the sensor 226 is a pressure sensor in fluid communication with an internal passageway 242 of the body 218. In the illustrated embodiment, the sensor 226 extends through a bore 240 formed in the body 218. In other embodiments, the body includes a port to fluidly communicate the pressure within the internal passageway to a sensor positioned outside of the body. In some embodiments, the pressure sensor measures pressure at a distal end of the device. In the illustrated embodiment, the pressure sensor 226 is positioned closer to the mouthpiece 14 than to the resistance portion 22. In some embodiments, the resistance portion 222 includes a sensor for measuring pressure (i.e., a pressure sensor). In other words, the sensor is positioned in the resistance portion in some embodiments. In such an embodiment, the sensor is integrally formed in one piece with the resistance portion (e.g., in a molding operation), or the resistance portion is made of multiple parts assembled together. In some embodiments, more than one sensor is included in the device. In other embodiments, more than one type of sensor is included in the device (e.g., a temperature sensor, a humidity sensor, a sound sensor, etc.).

The sensor 226 is configured to communicate electronically with the processor 234. In other words, the sensor 226 is in electronic communication with the processor 234. The processor (e.g., a processing unit, a microprocessor, a microcontroller, or other suitable programmable device) includes, among other things, a control unit, a memory (a non-transitory computer readable medium), input units, and output unit, an arithmetic logic unit ("ALC"), and a plurality of registers, and can be implemented using a known computer architecture (e.g., a modified Harvard architecture, a von Neumann architecture, etc.). The memory can include, for example, a program storage area and the data storage area. The program storage area and the data storage area can include combinations of different types of memory, such as a ROM, a RAM (e.g., DRAM, SDRAM, etc.), EEPROM, flash memory, a hard disk, a SD card, or other suitable magnetic, optical, physical, or electronic memory devices. The processor 234 is configured to communicate in a stand-alone and/or a distributed environment, and is configured to communicate via wired or wireless communications with other processors, where such one or more processor can be configured to operate on one or more processor-controlled devices that can be similar or different devices. Such devices and systems will be understood by a person of skill in the art and are not described in detail herein.

Figure 11:
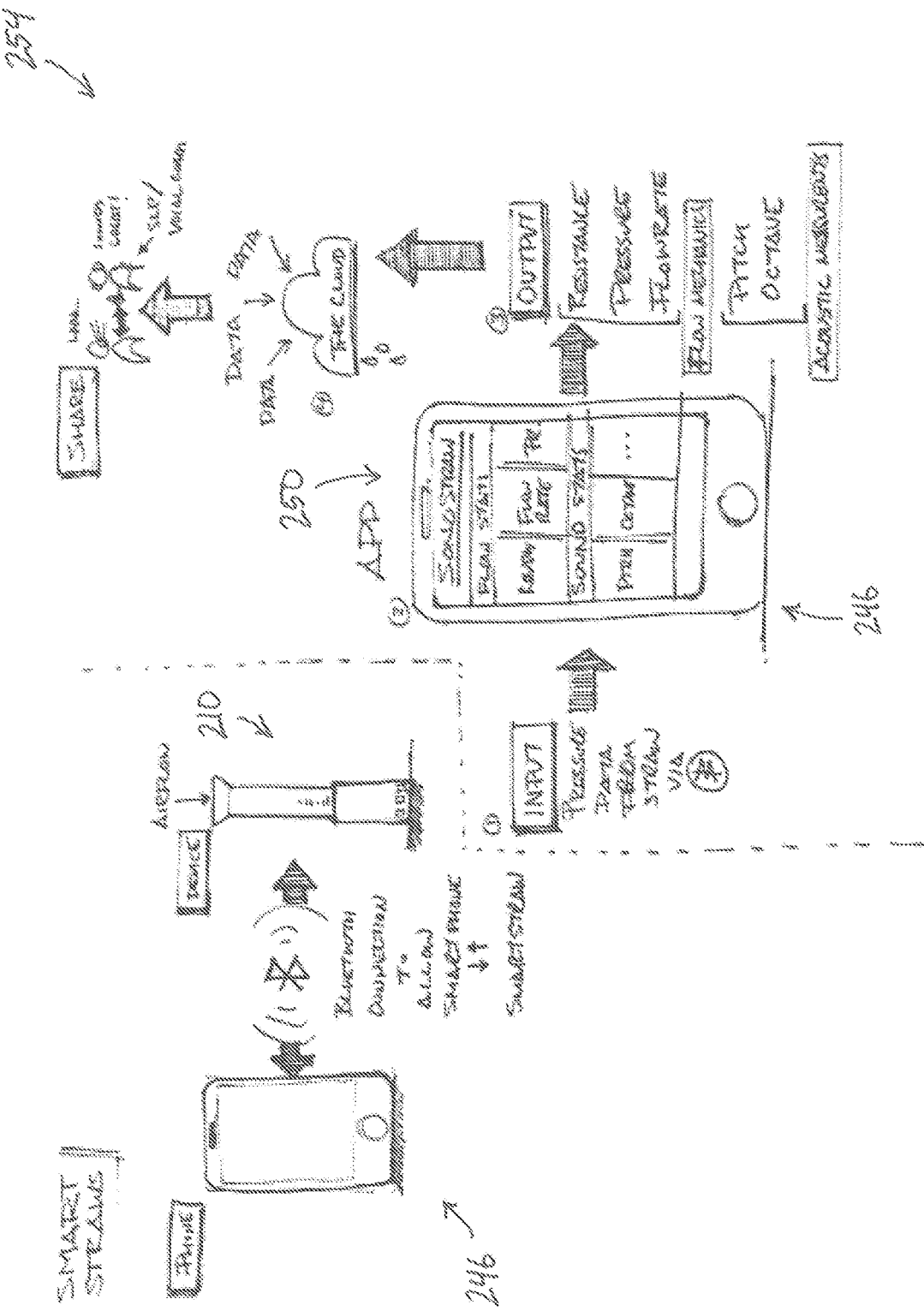
FIG. 11 is a schematic of a system for voice therapy including a device and a software application.

In some embodiments, the device 210 further includes a communication module 242 (FIG. 8) in electronic communication with the processor 234 for data transfer of the sensor 226 output, for example. In some embodiments, the communication module 242 is wireless. In some embodiments, the communication module 242 employs any suitable communications protocol, such as Wi-Fi, Bluetooth, ZigBee, etc. In some embodiments, the communication module 242 is built into a control board with the processor 234. With reference to FIG. 11, the device 210 wirelessly communicates with an external device or system 246 (a mobile phone, a PC, a network, etc.) via the communication module 242. In the illustrated embodiment, the external device 246 is a mobile cell phone that communicates via Bluetooth with the device 210 for bidirectional data exchange. The external device 246 monitors the device 210 and provides additional functionality such as data collection, data storage, visual display, analysis, feedback, iterative actions, etc.

Advantageously, the device 210 allows a user to select a specific desired airflow resistance, measure the pressure within the device 210, and provide quantifiable and repeatable results.

With continued reference to FIG. 11, another aspect of the present disclosure provides a computer application 250 and a voice therapy system 254. The system 254 includes a voice therapy device (e.g., the device 210) and the computer application 250 (also, "program" or "app") that provides information and guidance to the patient. The sensor 226 output is in electronic communication with the application 250 with a wired or wireless connection (e.g., Bluetooth).

The application 250 can take the form of hardware (including processors, memory devices, displays, mobile devices, etc.), software (including firmware, resident software, micro-code, app etc.) or an embodiment combining software and hardware aspects. In some embodiments, the application 250 is provided as an app for a handheld mobile device. Software included in the implementation of the methods or systems disclosed herein can be stored in the memory. The software includes, for example, firmware, one or more applications, program data, filters, rules, one or more program modules, and other executable instructions. For example, the computer can be configured to retrieve from the memory and execute, among other things, instructions related to the processes and methods described herein. Further, it is to be understood that, in some embodiments, the application 250 can be used with other conventional phonation devices, or it can be used as a standalone therapy with no phonation device.

The application 250 performs a wide variety of functions related to voice therapy, providing a holistic and cohesive training interface. Some example functions of the application include but are not limited to: providing and tracking patient exercises; providing training content and progress reports; sharing information between patients and clinicians; providing habit/behavior training and encouragement; recording exercise/training results in real time; and providing feedback to patient and clinician on applicable information such as training efficiency.

In some embodiments, the application 250 is used by patients and speech-language pathologists as part of a clinical voice therapy regimen. It may also be used as a standalone product for vocal professionals seeking better vocal health. Advantageously, the application 250 offers users a singular location to record, track, and share all activities related to vocal heath. The application 250 provides a range of functionality, including the following aspects.

In some embodiments, the application 250 provides vocal education. Some examples include: easy to understand explanations about the scientific basis of voice production; and anatomical illustrations and animations of larynx and vocal folds.

In some embodiments, the application 250 provides vocal analysis. Specifically, the application 250 provides tools to collect, analyze, store, export, and share vocal activities. Some examples include: recording and sharing exercises recommended for the patient by the clinician as audio or video files; recording and sharing exercises and training results by the patient; analysis of pitch ranges and formant frequencies; recording and sharing of app user's voice with option to share with clinician; and tools to communicate with clinician for feedback In some embodiments, the application 250 provides vocal rehab. Specifically, the application 250 provides vocal exercises and tools for voice habilitation/rehabilitation. Some examples include: tools for monitoring volume and pitch; exercises to complete with clinician and to repeat after clinician; and customizable exercise selection by clinician.

In some embodiments, the application 250 provides daily support. Specifically, the application 250 provides tools to support vocal hygiene, practice reminders, vocal lifestyle, and self-ratings. Some examples include: tracking patient adherence/compliance to exercise regimens; providing habit/behavior training regarding hydration, smoking, GERD and allergies; providing feedback on training efficiency and patient progress; journal tracking self-assessment and progress.

In some embodiments, the application 250 provides data collection. The application 250 enables the collection of data spanning tens of thousands of voice therapy patients, creating a mineable data set that can support research efforts, determine age-appropriate and gender-specific normative ranges, and health outcomes.

In some embodiments, the application 250 provides sensor data. As described herein, the device 210 communicates with the application 250 via the communication module 242 (e.g., an integrated Bluetooth chip. The pressure sensor 226 embedded in the device 210 sends data to the application 250, enabling the application 250 to record pressure readings from the device while the user is conducting exercises that are a part of their voice therapy regimen. Based on pressure readings, the application 250 can calculate resistance and flow rates. Results can be shared via a network (e.g., a cloud-based network), and the clinician (speech-language pathologist) can then utilize this information to quantifiably determine patient progress and outcomes. In some embodiments, the application 250 provides real-time user feedback based on the pressure sensor 226 data.

Figure 12A:
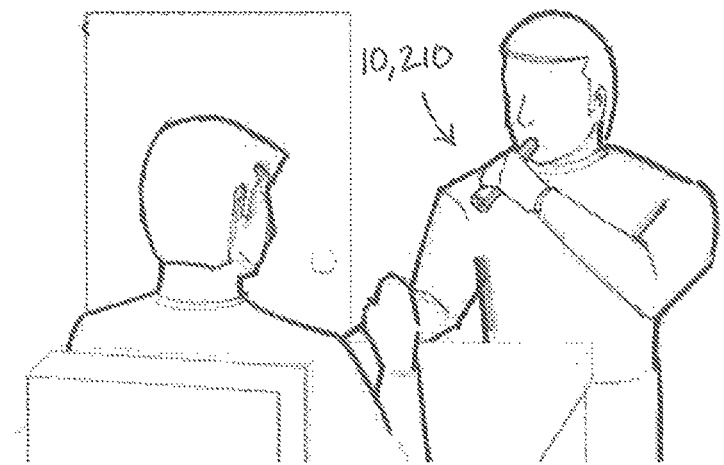
FIG. 12A is a schematic of a first use scenario of a device for voice therapy.
Figure 12B:
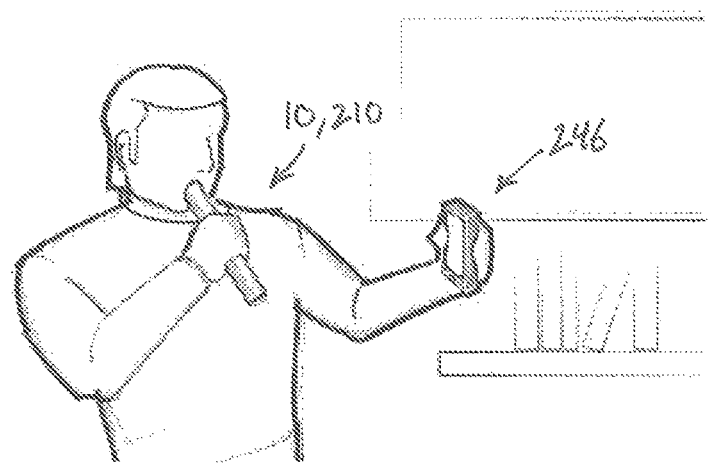
FIG. 12B is a schematic of a second use scenario of a device for voice therapy.
Figure 12C:
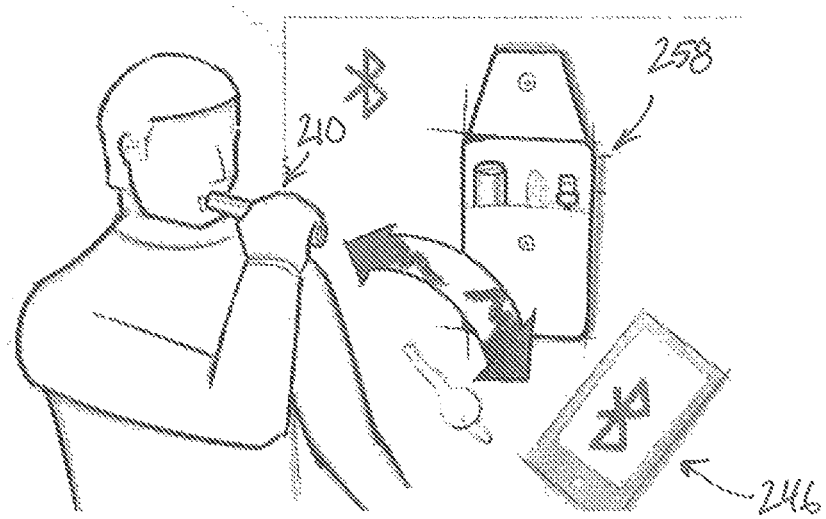
FIG. 12C is a schematic of a third use scenario of a device for voice therapy.

With reference to FIGS. 12A-12C, the device 210 is used in various scenarios. With reference to FIG. 12A, the device 210 can be used by a patient with or without the guidance and instruction of a speech pathologist. With reference to FIG. 12B, the device 210 can be used in a passive mode where the application 250 is used, for example, to provide therapeutic input such as: exercise instructions, timers, focusing imagery, reminders, checklists, fillable forms, and the like. With reference to FIG. 12C, the device 210 can be used in a dynamic mode where the sensor 226 provides air pressure information to application 250, which is then used to provide adaptive interactions with the user/patient. In some embodiments, the dynamic mode can also provide information to a clinician or voice therapist. This allows the user to interact with the clinician in real time, even if the user is remote from the clinician.

According to another aspect of the present disclosure, device 210 (or device 10) can be provided in a kit 258 of parts (see, e.g., FIG. 12C). The kit 258 can include at least one mouthpiece (e.g., mouthpiece 214), at least one body (e.g., body 218), and at least one resistance portion (e.g., resistance portion 222). In some embodiments, the kit 258 includes cleaning accessories, a carrying case, and a charger.

Another aspect of the present disclosure provides a method of voice therapy using the disclosed device. A prescribed airflow resistance can be selected from an available range using reference markings on the device (e.g., indicia 114). A user or patient can then perform exercises by exhaling/phonating into the mouthpiece (e.g., mouthpiece 14) in a prescribed manner. The resistance can be dynamically adjusted as desired during the exercise session.

One skilled in the art will readily appreciate that the present disclosure is well adapted to carry out the objects and obtain the ends and advantages mentioned, as well as those inherent herein. The present disclosure described herein are exemplary embodiments and are not intended as limitations on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

Various features and advantages are set forth in the following claims.

What is claimed is:

1. A voice therapy device, comprising:
a body having an internal passageway with a longitudinal axis that defines an airflow direction;
a mouthpiece positioned at a proximal end of the body; and
a resistance portion positioned at a distal end of the body, wherein the resistance portion includes a blocking structure and one or more airflow outlets; and wherein the blocking structure is conical and symmetrical about the longitudinal axis; wherein the blocking structure extends into the internal passageway through an opening in the distal end of the body; and
wherein the resistance portion including the blocking structure rotates relative to the body about the longitudinal axis to adjust an open area between the resistance portion and the body to vary an airflow resistance through the internal passageway.

2. The device of claim 1, wherein the one or more airflow outlets are oriented perpendicular to the longitudinal axis.

3. The device of claim 1, wherein a height of the blocking structure is greater than a widest diameter of the blocking structure.

4. The device of claim 1, wherein the resistance portion is a cap positioned at least partially around the body.

5. The device of claim 1, wherein the device is configured to provide backpressure to a user's vocal folds during phonation.

6. The device of claim 1, wherein the mouthpiece and the resistance portion are removably coupled to the body.

7. The device of claim 1, wherein the airflow resistance is continuously adjustable between a minimum resistance and a maximum resistance.

8. The device of claim 1, comprising a threaded connection between the resistance portion and the body.

9. The device of claim 1, wherein the body includes indicia representing a level of the airflow resistance, and wherein the resistance portion includes an indicator corresponding to the indica.

10. The device of claim 1, further comprising a pressure sensor in fluid communication with the internal passageway and in electronic communication with a processor.

11. The device of claim 10, wherein the processor is coupled to a first mount formed on the body, and a battery is coupled to a second mount formed on the body; and further comprising a wireless communication module in electronic communication with the processor.

12. A system for voice therapy, comprising a device according to claim 1 and a software application.

13. The system of claim 12, wherein the software application comprises at least one of vocal education tools; vocal analysis; vocal rehabilitation tools, and vocal lifestyle support features.

14. The system of claim 12, wherein the software application provides real time user feedback based on pressure sensor data; and wherein the software application is on an external device.

15. A method of voice therapy, comprising performing prescribed phonation using a device according to claim 1.

16. The device of claim 1, wherein the open area is defined between the blocking portion and a lip at the distal end of the body.

17. The device of claim 1, further comprising a first flange positioned on an outer surface of the body and a second flange positioned on an inner surface of the resistance portion; and wherein the second flange abuts the first flange when the resistance portion is adjusted to a maximum open position.

18. The device of claim 1, wherein the one or more airflow outlets are oriented perpendicular to the longitudinal axis; and wherein the resistance portion is a cap positioned at least partially around the body.

19. The device of claim 18, wherein the one or more airflow outlets are positioned radially outward from the blocking structure relative to the longitudinal axis.

20. The device of claim 19, wherein the open area is defined between the blocking portion and a lip at the distal end of the body; further comprising a threaded connection between the resistance portion and the body; wherein the airflow resistance is continuously adjustable between a minimum resistance and a maximum resistance.

\* \* \* \* \*